(12) United States Patent
Bush

(10) Patent No.: US 8,623,403 B2
(45) Date of Patent: Jan. 7, 2014

(54) METHODS FOR REGULATING GELATION OF HYDROGEL SOLUTIONS AND USES THEREOF

(75) Inventor: Joshua R. Bush, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/512,250

(22) PCT Filed: Nov. 30, 2010

(86) PCT No.: PCT/US2010/058272
§ 371 (c)(1),
(2), (4) Date: Sep. 25, 2012

(87) PCT Pub. No.: WO2011/068774
PCT Pub. Date: Jun. 9, 2011

(65) Prior Publication Data
US 2013/0195921 A1   Aug. 1, 2013

Related U.S. Application Data

(60) Provisional application No. 61/265,879, filed on Dec. 2, 2009.

(51) Int. Cl.
*A61F 13/00*   (2006.01)

(52) U.S. Cl.
USPC .......................................... 424/443; 424/422

(58) Field of Classification Search
None
See application file for complete search history.

(56) References Cited

U.S. PATENT DOCUMENTS

| 5,071,644 A * | 12/1991 | Viegas et al. ............... 514/772.7 |
| 5,620,706 A * | 4/1997 | Dumitriu et al. ............. 424/485 |
| 6,486,285 B2 * | 11/2002 | Fujita ............................. 527/312 |
| 2009/0270514 A1 * | 10/2009 | Laurencin et al. ............ 514/769 |

* cited by examiner

*Primary Examiner* — Susan Tran
(74) *Attorney, Agent, or Firm* — Rodney L. Sparks

(57) ABSTRACT

The present invention provides a method for preparing chitosan and xylan composite thereto-gelling solutions to allow regulating the conditions in which the chitosan and xylan solution will gel. The present invention also provides methods for using chitosan/xylan solutions as compositions and for using chitosan/xylan solutions in vitro and in vivo. A thermally-responsive composite hydrogel has been developed and synthesized from the natural polymers chitosan and xylan. The new material is a viscous liquid at room temperature, but turns to a solid gel at physiological temperature (37 C). Rate of gelation is controlled with addition of a salt solution. Applications are for tissue engineering and local delivery of therapeutic agents, including proteins and drugs, as wells as cells.

19 Claims, 6 Drawing Sheets

METHODS FOR REGULATING GELATION OF HYDROGEL SOLUTIONS AND USES THEREOF

CROSS REFERENCE TO RELATED APPLICATIONS

This application is a national stage filing of International Application No. PCT/US2010/058272, filed Nov. 30, 2010, which claims priority under 35 U.S.C. 119(e) from U.S. Provisional Application Ser. No. 61/265,879, filed Dec. 2, 2009, entitled "Methods for Regulating Gelation of Hydrogel Solutions and uses Thereof," which is hereby incorporated by reference herein in its entirety.

FIELD OF THE INVENTION

The present invention relates generally to a biocompatible temperature-dependent gelling solution of chitosan and inorganic salts, and methods of preparation and use thereof.

BACKGROUND

Chitin is a naturally abundant mucopolysaccharide which is a (1-4)-β-linked glycan composed of 2-acetamido-2-deoxy D-glucose. Application of chitin is currently limited because of its low solubility in most common organic solvents.

On the other hand, chitosan, which is the N-deacetylated derivative of chitin obtained by the partial or total alkaline deacetylation of chitin, is soluble in acidic aqueous solutions. Chitosan is composed primarily of 2-acetamido-2-deoxy D-glucose and glucosamine residues the aqueous solubility can be attributed to the protonation of the amino groups in acidic environments. It is a pH dependent cationic polysaccharide, which is known to be non-toxic, biocompatible, and biodegradable, with its degradation products being known natural metabolites. Chitosan has been evaluated in a number of medical applications including wound dressings, matrices for controlled drug delivery and as a hemostatic agent.

Chitosan is an N-deacetylated derivative of chitin which is the structural component of crustacean shells and fungal cell walls, and is obtained at a low cost from sea-food processing (Chitin: Fulfilling a Biomaterials Promise: Eugene Khor, Elsevier, Oxford, UK, 2001). The structure of chitin and chitosan are similar to cellulose where, carbon-2 of the cellulose has acetamide or amino groups, for chitin and chitosan respectively. Chitosan is an inert, hydrophilic, biocompatible, and biodegradable polymer and hence are attractive candidates for biomedical and pharmaceutical applications. Chitosan is currently investigated for various applications such as topical ocular application, as a bioadhesive polymer, penetration enhancer by opening epithelial tight-junctions and as wound dressing (Berger, et al., European Journal of Pharmaceutics and Biopharmaceutics 57 (2004) 19-34).

Various chemically modified chitosan derivatives with unique properties have been developed (Hitoshi et al., Prog. Polym. Sci. 29 (2004) 887-908). The excellent biocompatibility of chitosan, combined with its enzymatic biodegradability, makes chitosan an excellent candidate for various in vivo applications. In addition, the low cost of chitosan and its wide availability as a natural waste product, makes chitosan a very attractive polymer for wide range of applications.

Chitosan has been extensively investigated for developing hydrogels with unique properties, due to the hydrophilicity of the base polymer, and the availability of active cross-linkable groups along the polymer chain. These chitosan hydrogels were found to be excellent candidates for a variety of applications, including, controlled release of bioactive/drug molecules, as cell encapsulation matrices, and as tissue engineering scaffolds. Chemical or covalent cross-linking of chitosan making use of mainly the active amino groups along the polymer chain and ionic cross-linking making use of the cationic nature of chitosan aqueous acid solutions, have been extensively investigated for developing hydrogels for various applications.

The different chemical cross-linking agents reported for chitosan include dialdehydes such as glutaraldehyde, diethyl squarate, oxalic acid, and genipin. Apart from these small molecules, functionalized biopolymers such as poly(ethylene glycol diacrylate), oxidized cyclodextrin, telechelic-PVA, PEG dialdehydes and scleroglucan have also been investigated.

In addition to covalent cross-linking, polyelectrolyte complexes of chitosan with a wide range of anionic polymers mainly chitosan alginate system have been extensively investigated for developing drug delivery systems and porous scaffolds for tissue engineering and wound dressings.

Ionic cross-linking of chitosan has been extensively investigated, because it is a simple and mild process with no auxiliary catalyst requirements, and such a procedure has important ramifications for biomedical applications. Metallic anions such as Mo(VI) and Pt(II) have been extensively investigated for ionic cross-linking. Various anions such as sulfates, citrates, oxalates, polyphosphates, and also calcium phosphate, have been tested for the ability to form ionically cross-linked gels with chitosan. All of these ions induce the formation of pure ionic cross-linking, where the chitosan solution instantaneously becomes a gel in the presence of these ions, due to the spontaneity of the ionic reactions.

Temperature and pH sensitive gelling systems comprising chitosan are known (Laurencin et al., PCT App. No. PCT/US2007/001896; Chemte et al., U.S. Pat. No. 6,344,488). Recently a temperature and pH sensitive gelling system was developed using chitosan in the presence of β-glycerophosphate. In addition to β-glycerophosphate, corresponding sulfates and monosaccharide derivatives were found to exhibit the characteristic properties of β-glycerophosphate (Chemte et al., U.S. Pat. No. 6,344,488; Chemte et al., Biomaterials 21 (2000) 2155-2161; Ruel-Gariepy et al., European Journal of Pharmaceutics and Biopharmaceutics, 57 (2004) 53-63; Ruel-Gariepy et al., J Controlled Release. 82 (2002) 373-383; Molinaro et al., Biomaterials 23 (2002), 2717-2722). Others have made hydrogels with various components, including xylan, but have not made temperature and pH sensitive gelling systems for use in vivo (Gabrielii I, P. Gatenholm P. "Preparation and properties of hydrogels based on hemicellulose," Journal of Applied Polymer Science 69, 1661-1667 (1998); Gabrielii I, et al. "Separation, characterization and hydrogel-formation of hemicellulose from aspen wood," CARBOHYDRATE POLYMERS 43(4), 367-374 (2000); Tanodekaew S, et al. "Xylan/polyvinyl alcohol blend and its performance as a hydrogel," Journal of Applied Polymer Science 100(3), 1914-1918 (2006)).

Injectable in situ forming hydrogels are receiving considerable attention for a variety of biomedical applications such as sustained drug delivery, cell encapsulation and as scaffolds for tissue engineering (Tae et al., Biomaterials, 26, 5259-66, 2005). An injectable system offers several advantages including conformal matching of the implant to complex tissue shapes, delivery of large volumes of implant via minimally invasive surgery, improved patient compliance and comfort, and allows for the delivery of sensitive biomolecules and living cells because it is a gentle process. In situ forming hydrogels are potential candidates specifically for developing sustained delivery vehicles for therapeutic proteins with short half lives.

Various materials have been investigated for the development of injectable hydrogel systems based on non-degradable synthetic polymers such as poloxamers, N-isopropylacrylamide and a variety of degradable natural polymers (Hatefi and Amsden, J. Control Rel., 80:9-28, 2002). One of the most extensively investigated natural polymers for hydrogel development is chitosan. Chitosan is an N-acetylated derivative of the natural polymer Chitin. Chitin is the structural component of crustacean shells and fungal cell walls and is the second most abundant natural polymer. Due to the excellent biocompatibility and enzymatic degradability of chitosan, hydrogels based on chitosan have been found to be excellent candidates for a variety of medical and pharmaceutical applications (Berger et al., Eur. J. Pharm. Bio Pharm., 57:19-34, 2004). Grafting poly(ethylene glycol) of appropriate molecular weight to chitosan has been shown to act as a thermogelling system (Bhattarai et al., J. Control Rel. 103:609-624). Other methods and compositions for preparing hydrogels are also known (Laurencin et al., PCT App. No. PCT/US2007/001896; Chemte et al., U.S. Pat. No. 6,344,488).

There is a long felt need in the art for compositions and methods to prepare and use biocompatible solutions comprising chitosan for better hydrogel solutions which can be injected or directly applied in vivo. The present invention satisfies these needs.

SUMMARY OF THE INVENTION

The present invention is based on the discovery disclosed herein that the natural polysaccharide xylan can be used as a component of a hydrogel and that the rate of gelation can be controlled by the addition of salt. To that end, a thermally-responsive composite hydrogel has been developed and synthesized from natural polymers. That is, a novel injectable thermo-gelling polysaccharide system that can set into a hydrogel at physiological temperature has been developed. The new material is a viscous liquid at room temperature, but turns to a solid gel at physiological temperature (37° C.). The rate of gelation is controlled with addition of a salt solution and by varying the amount of components or the temperature. One application of this material is for tissue engineering, to provide a medium for tissue and cellular growth and to provide a carrier for delivery of therapeutic agents including proteins, peptides, and other molecules and drugs.

The chitosan/xylan thermogelling solution of the invention has the potential for immediate impact in areas such as orthopedic surgery, where the gel could be delivered to critical injuries without significant alteration of current surgical techniques. The thermally-responsive, in situ gelling behavior coupled with the ability to deliver active therapeutic agents such as proteins make the use of this material a significant step forward in treating traumatic injuries such as non-union fractures and osteolytic bone lesions.

In one embodiment, the present invention provides a thermo-gelling solution comprising xylan, chitosan, a salt, and optionally an acid, wherein when the solution is prepared, it is a solution at a pH between about 6.0 and about 8.0 and at a temperature below about 30° C., further wherein when the temperature is increased gelation of the solution occurs more rapidly or when the salt is added gelation occurs more rapidly.

In one aspect, the ratio of chitosan to xylan is about 3 to 1 by weight. In one aspect, when the chitosan used is 85% deacetylated ultrapure chitosan, the total amount of chitosan and xylan added is about 16 mg/ml. In another aspect, when the chitosan used is 78.9% deacetylated ultrapure chitosan, the total amount of chitosan and xylan added is about 14.4 mg/ml. In one aspect, gelation of the solution occurs within a temperature range from about 20° C. to about 50° C. In another aspect, gelation occurs at about 37° C. As described herein, the rate of gelation can be varied by temperature and by the amount of salt added as well as when the salt is added.

In one aspect, gelation occurs in less than about 1 hour when the temperature of the thermogelling solution is increased to about 37° C. In another aspect, gelation occurs in less than about 30 minutes when the temperature of the thermogelling solution is increased to about 37° C. In yet another aspect, gelation occurs in less than about 10 minutes when the temperature of the thermogelling solution is increased to about 37° C. In a further aspect, gelation occurs in less than about 5 minutes when the temperature of the thermogelling solution is increased to about 37° C.

In one embodiment, the salt is an inorganic salt.

In one embodiment, the salt is ammonium hydrogen phosphate or sodium pyruvate.

In one aspect, when the salt is ammonium hydrogen phosphate, the thermo-gelling solution comprises a ratio of chitosan to ammonium hydrogen phosphate between about 1.0 and about 3.5.

In one aspect, when the salt is ammonium hydrogen phosphate, the concentration of salt is about 20 mg/ml and the molarity of salt is about 15 mmol/l.

In one aspect, the thermo-gelling solution further comprises an aqueous acidic solution.

In one aspect, the thermo-gelling solution comprises acetic acid at a concentration from about 0.25% v/v to about 0.5% v/v.

In one aspect, the chitosan used has a molecular weight of between about 20,000 and about 500,000. In another aspect, the chitosan has a molecular weight of about 429,000.

In one aspect, the thermo-gelling solution is biocompatible.

The invention further provides a pharmaceutical composition comprising the thermo-gelling solution of the invention, a pharmaceutically-acceptable carrier, and optionally an effective amount of at least one cell, material, drug, therapeutic agent, or compound useful for treating an injury, disease, or disorder.

The invention further provides a method of preparing a thermo-gelling solution comprising xylan, chitosan and salt. The methods comprises adding the desired amount of xylan to deionized water and heating to dissolve the xylan, forming a xylan solution. The xylan solution is then cooled and optionally acidified adding acid. In one aspect, the acid is acetic acid. Then the desired amount of chitosan is added to the cooled xylan solution and dissolved the xylan solution, forming a xylan/chitosan solution. Then the desired amount of salt is added to the xylan/chitosan solution and the salt is dissolved, forming a thermo-gelling solution comprising xylan, chitosan and salt. In one aspect, the salt can be added just prior to use of the thermo-gelling solution, as can cells, materials, and compounds.

In one aspect, the xylan is dissolved by heating to about 85° C. In one aspect, the heated xylan solution is cooled to about room temperature after the xylan is dissolved. In one aspect, the xylan solution is cooled to about 20° C. to about 25° C. after said xylan is dissolved.

In one aspect, when chitosan is added it is allowed to dissolve for about 12 to about 24 hours before salt is added.

In one aspect, the ratio of chitosan to xylan is about 3 to 1 by weight.

In one aspect, when the chitosan used is 85% deacetylated ultrapure chitosan, the total amount of chitosan and xylan is about 16 mg/ml. In another aspect, when the chitosan used is 78.9% deacetylated ultrapure chitosan, the total amount of chitosan and xylan is about 14.4 mg/ml.

In one aspect, the salt is an inorganic salt.

In one aspect, the salt is ammonium hydrogen phosphate or sodium pyruvate.

In one aspect, when the salt is ammonium hydrogen phosphate, the thermo-gelling solution comprises a ratio of chitosan to ammonium hydrogen phosphate between about 1.0 and about 3.5.

In one aspect, when the salt is ammonium hydrogen phosphate, the concentration of salt is about 20 mg/ml and the molarity of the salt is about 15 mmol/l.

In one aspect, the amount of acetic acid used is from about 0.25% v/v to about 0.5% v/v.

In one aspect, the chitosan has a molecular weight of between about 20,000 and about 500,000. In another aspect, the chitosan has a molecular weight of about 429,000.

The present invention further provides compositions and methods for treating an injury, disease, or disorder in a subject. In one embodiment, the method comprises administering to a subject a pharmaceutical composition comprising a thermo-gelling solution of the invention and an effective amount of at least one cell, material, or compound useful for treating the injury, disease, or disorder.

The present invention further provides additional compositions and methods for treating an injury, disease, or disorder in a subject. In one embodiment, the invention provides a method for treating an injury, disease, or disorder in a subject in need thereof, comprising administering to the subject a thermogelling-solution of the invention comprising an effective amount of at least one cell, material, or compound useful for treating said injury, disease, or disorder.

In one aspect, the injury, disease, or disorder is a musculoskeletal-associated injury, disease or disorder.

In one aspect, the material or compound is selected from the group consisting of drugs, antimicrobial agents, peptides, growth factors, cytokines, nucleic acids, drugs, matrix components, and imaging agents.

In one aspect, the material or compound is at least one peptide selected from the group consisting of R1, L7, and bone morphogenic protein-2.

In one aspect, a cell type useful for treatment, includes, but is not limited to, a cell selected from the group consisting of stem cells, pluripotent stem cells, committed stem cells, embryonic stem cells, adult stem cells, bone marrow stem cells, bone marrow-derived stem cells, adipose stem cells, mesenchymal stem cells, umbilical cord stem cells, dura mater stem cells, precursor cells, differentiated cells, osteoblasts, osteoclasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons.

In one aspect, the cell is a human cell.

In one embodiment, the thermo-gelling solution is added to a scaffold before administration to a subject. In one aspect, the scaffold is a microsphere. In one aspect, the microsphere is a PLGA microsphere.

In one aspect, a subject of treatment is a human.

The invention further provides compositions and methods for delivering a cell, material or compound to a subject in need thereof, comprising administering to the subject a thermo-gelling solution of the invention, wherein the thermo-gelling solution further comprises a cell, material, or compound.

The invention further provides compositions and methods for delivering a cell, material or compound to a subject in need thereof, comprising administering to the subject a pharmaceutical composition a thermo-gelling solution of the invention, wherein the pharmaceutical composition further comprises a cell, material, or compound.

In accordance with the present invention, there is also provided a pharmaceutical composition comprising a thermo-gelling solution of chitosan, xylan and salts and insoluble solid particulates or water-soluble substances. There is also provided a method for administering the pharmaceutical composition comprising injecting or applying the pharmaceutical composition.

In one embodiment, the invention provides a method of delivering the thermo-gelling solution as an injectable scaffold for tissue engineering comprising injecting an effective amount of the thermo-gelling solution.

The invention further provides a method for delivering one or more substances from the group consisting of cells, fibroblasts, chondrocytes, osteogenic cells, stem cells, genes, drugs, proteins, chemicals, bioactive molecules, growth factors, and therapeutic proteins and peptides comprising administering the thermo-gelling solution as an injectable matrix for the delivery of these substances.

The invention still further provides a method for providing the thermo-gelling solution as an injectable plug for therapeutic embolization and chemoembolization comprising injecting the thermo-gelling solution as an injectable plug for therapeutic embolization and chemoembolization.

BRIEF SUMMARY OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 4, comprising FIGS. 4A-4B, demonstrates micrographically mineralized bone formed in the thigh muscle of a rat-images with ∓CT at 4 weeks. BMP-2 was delivered from the chitosan/xylan composite thermogel at this ectopic site. 0.25∓g/∓L was delivered in a 40∓L injection of the thermogel. 4A—ectopic bone in thigh muscle. 4B—enlarged image with higher threshold value to focus on hard tissue.

DETAILED DESCRIPTION OF THE INVENTION

Figure 1:
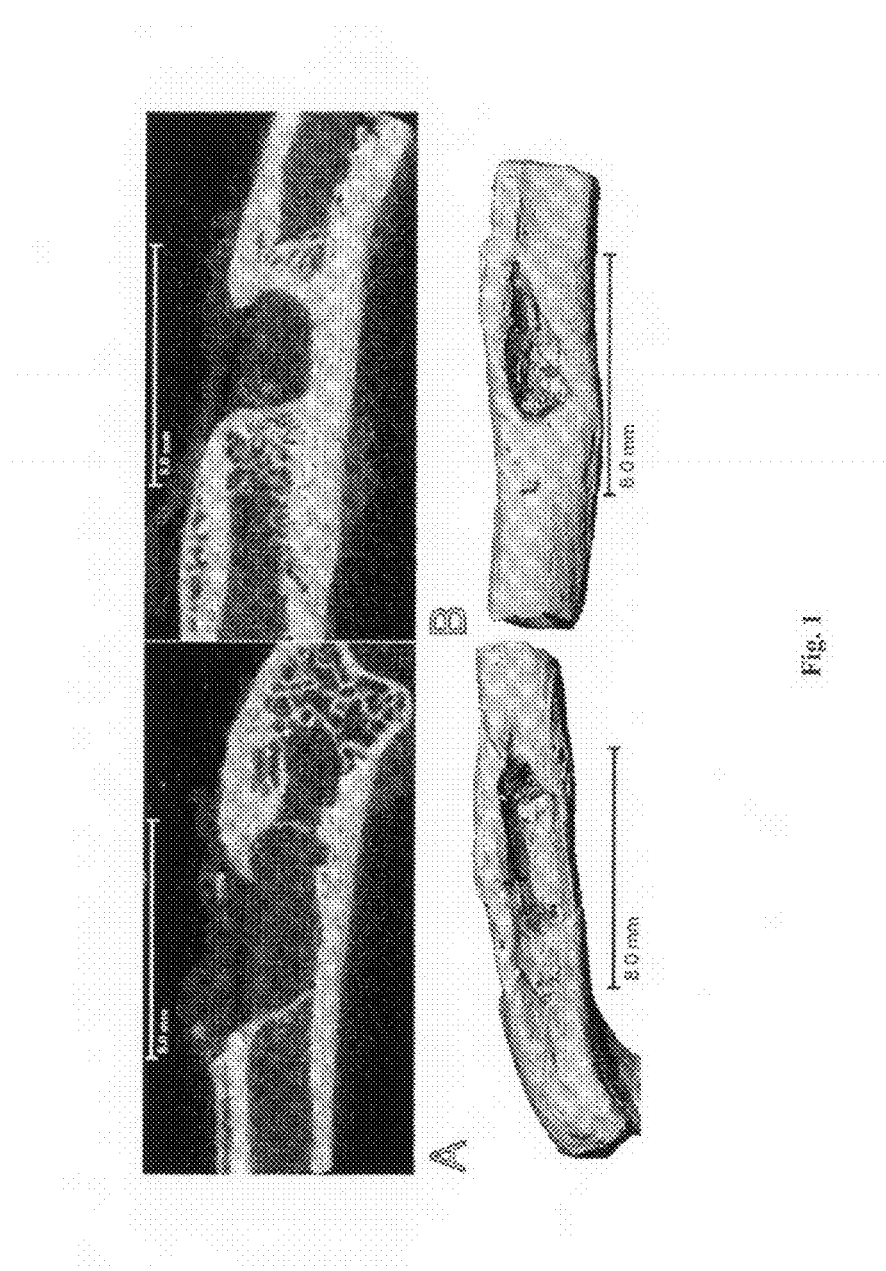
FIG. 1, comprising FIGS. 1A-1B (four panels), demonstrates micrographically the results of experiments in which unicortical critical sized defects in rat femurs were treated with osteogenic peptides delivered from a thermally-responsive hydrogel made from ultrapure chitosan (no xylan). The hydrogel successfully delivered the growth factors and allowed healing to progress across the defect from 1A) five weeks to 1B) eight weeks. Images created by ±CT with a VivaCT 40 scanner from ScancoMedical.

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for radicals, substituents, and ranges are for illustration only; they do not exclude other defined values or other values within defined ranges for the radicals and substituents.

ABBREVIATIONS AND ACRONYMS

AHP— ammonium hydrogen phosphate
BMP-2—bone morphogenetic protein-2
BSA—bovine serum albumin
DMEM—Dulbecco's modified Eagle's medium
ECM—extracellular matrix
ES—embryonic stem cell
FACS—fluorescent activated cell sorting
FAF—fatty acid free
FBS—fetal bovine serum
FGF—fibroblast growth factor
gf—growth factor
H&E—hematoxylin and eosin
HS—human serum (also referred to as HmS herein)
HSA—human serum albumin
ODM—osteogenic medium
PCR—polymerase chain reaction

DEFINITIONS

As used herein, the singular forms "a," "an," and "the" include plural reference unless the context clearly dictates otherwise.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, hypertension and diabetes. The additional compounds may also be used to treat symptoms associated with the injury, disease or disorder, including, but not limited to, pain and inflammation. Such compounds or agents include, but are not limited to drugs, antimicrobials, growth factors, cytokines, etc.

The term "adult" as used herein, is meant to refer to any non-embryonic or non-juvenile subject. For example the term "adult adipose tissue stem cell," refers to an adipose stem cell, other than that obtained from an embryo or juvenile subject.

A disease, condition, or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

"Antiviral agent," as used herein means a composition of matter which, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, Retrovir® Glaxo Wellcome Inc., Research Triangle Park, NC) is an antiviral agent which is thought to prevent replication of HIV in human cells.

The term "autologous", as used herein, refers to something that occurs naturally and normally in a certain type of tissue or in a specific structure of the body. In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbecco's Modified Eagle's Medium, Ham's F12, Eagle's Medium, RPMI, AR8, etc., to which other ingredients may be added. The term does not exclude media which have been prepared or are intended for specific uses, but which upon modification can be used for other cell types, etc.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system and/or chemically incorporated into the biological system.

The term "bioresorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year.

As used herein "burn" or "burns" refer to any detectable injury to tissue caused by energy applied to the tissue. The terms "burn" or "burns" further refer to any burning, or charring of the tissue, including thermal burns caused by contact with flames, hot liquids, hot surfaces, and other sources of high heat as well as steam, chemical burns, radiation, and electrical burns. First degree burns show redness; second degree burns show vesication; third degree burns show necrosis through the entire skin. Burns of the first and second degree are partial-thickness burns, those of the third degree are full-thickness burns.

The term "clearance," as used herein refers to the physiological process of removing a compound or molecule, such as by diffusion, exfoliation, removal via the bloodstream, and excretion in urine, or via sweat or other fluid.

A "compound," as used herein, refers to any type of substance or agent that is commonly considered a drug, or a candidate for use as a drug, as well as combinations and mixtures of the above.

The terms "comprising", "having", "including", and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

A "control" subject is a subject having the same characteristics as a test subject, such as a similar type of dependence, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test" subject is a subject being treated.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "decreased blood flow", as used herein, refers to a decrease in blood flow at a site of injury, disease, or disorder, and includes, but is not limited, a decrease in flow rate, an increase in stasis, and an increase in sludging in the vessels.

The term "delivery vehicle" refers to any kind of device or material, which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

A "disease" is a state of health of an animal wherein the animal cannot maintain homeostasis, and wherein if the disease is not ameliorated then the animal's health continues to deteriorate. As used herein, normal aging is included as a disease.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "enhancing bone repair" as used herein refers to methods of speeding up or inducing better bone repair using compounds of the invention, relative to the speed or amount of bone repair that occurs without administration of compounds of the invention.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

"Graft" refers to any free (unattached) cell, tissue, or organ for transplantation.

"Allograft" refers to a transplanted cell, tissue, or organ derived from a different animal of the same species.

"Xenograft" refers to a transplanted cell, tissue, or organ derived from an animal of a different species.

The term "growth factor" as used herein means a bioactive molecule that promotes the proliferation of a cell or tissue. Growth factors useful in the present invention include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue.

The term "improved blood flow," as used herein, refers to increased blood flow in a subject being treated according to the methods of the invention compared with the flow in a subject with an otherwise identical injury or condition not being treated according to the methods of the invention. Improved flow is determined by methods such as those described herein and can include less stasis, less sludging, or a combination of both, in the subject being treated compared with the untreated subject.

The term "ingredient" refers to any compound, whether of chemical or biological origin, that can be used in cell culture media to maintain or promote the proliferation, survival, or differentiation of cells. The terms "component," "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, "injury" generally refers to damage, harm, or hurt; usually applied to damage inflicted on the body by an external force.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a subject. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "in situ gelation" refers herein to the thermogelling of chitosan/phosphate gels once the chitosan/phosphate solution is administered within specific sites of a subject. Such sites include, but are not limited to, any tissues, body cavities, muscles, fractures or bone defects, ligaments, cartilages or organs. The thermogelling of the chitosan/phosphate solution is induced by the physiological temperature. Used interchangeably herein are the terms "isolate" and "select".

The term "isolated", when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays, which distinguish cell types.

An "isolated nucleic acid" refers to a nucleic acid segment or fragment, which has been separated from sequences, which flank it in a naturally occurring state, e.g., a DNA fragment that has been removed from the sequences, which are normally adjacent to the fragment, e.g., the sequences adjacent to the fragment in a genome in which it naturally occurs. The term also applies to nucleic acids, which have been substantially purified, from other components, which naturally accompany the nucleic acid, e.g., RNA or DNA, or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, Antibodies, *a Laboratory Manual*, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to either a molecule that joins two other molecules covalently or noncovalently, e.g., through ionic or hydrogen bonds or van der Waals interactions.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term 'material", as used herein, refers to synthetic and natural materials such as matrix components. The term "materials and compounds" as used herein, refers to, inter alia, materials, compounds, cells, peptides, nucleic acids, drugs, matrix components, and imaging agents.

The term "metal surface", as used herein, refers to any metal surface, including films, which can be used to deposit or apply polymers or metallic nanoparticles encompassed by the present invention.

A "mold" is a frame or model that shapes the gel system. Gels can be produced in, but are not limited to, glass or plastic-beakers, dishes, tubes or between two plates so as to obtain any expected shape.

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "musculoskeletal" as used herein encompasses the general broad meaning of the term, i.e., an organ system that gives a subject the ability to physically move, by using the muscles and skeletal system. Apart from locomotion, the skeleton also lends support and protects internal organs. Musculoskeletal diseases include, but are not limited to, diseases of the muscles and their associated ligaments, and other connective tissue and of the bones and cartilage viewed collectively. Musculoskeletal disorders include, for example, problems such as low back pain, joint injuries and repetitive strain injuries of various sorts.

The term "nanoparticle" or "particle" refers to a particle of any shape having the size of up to about 100 nanometers.

"Osteogenesis" as used herein refers to bone growth, bone remodeling, and repair of bone due to injury or disease.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer". The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The term "prevent," as used herein, means to stop something from happening, or taking advance measures against something possible or probable from happening. In the context of medicine, "prevention" generally refers to action taken to decrease the chance of getting a disease or condition.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "reversibly implantable" device is one which may be inserted (e.g. surgically or by insertion into a natural orifice of the animal) into the body of an animal and thereafter removed without great harm to the health of the animal.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

As used herein, "scaffold" refers to a supporting framework, such as one for bone or tissue growth, either in vivo or in vitro.

The term "skin," as used herein, refers to the commonly used definition of skin, e.g., the epidermis and dermis, and the cells, glands, mucosa, and connective tissue which comprise the skin.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured. Internal standards are often but are not limited to, a purified marker of interest which has been labeled, such as with a radioactive isotope, allowing it to be distinguished from an endogenous substance in a sample.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of diagnosis or treatment is a mammal, including a human.

As used herein, a "subject in need thereof" is a patient, animal, mammal, or human, who will benefit from the method of this invention.

A "surface active agent" or "surfactant" is a substance that has the ability to reduce the surface tension of materials and enable penetration into and through materials.

Before the present compositions and methods are described, it is to be understood that this invention is not limited to the particular processes, compositions, or methodologies described, as these may vary.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "thermal injury" is used interchangeably with "thermal burn" herein.

A "thermal-sensitive" gel system undergoes a phase transition when induced by temperature.

As used herein, "thermo-gelling" refers to the formation of a colloidal gel from solution as temperature increases.

The term "three-dimensional" refers to the fact that the chitosan solution is simultaneously gelled and shaped by the mold wherein the solution was initially poured.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "tissue injury-associated decreased blood flow", as used herein, refers to the decrease in blood flow which occurs following an injury, such as a thermal injury, to a tissue. The decrease in blood flow includes, but is not limited to, decreased volume, rate, stasis, or sludging. One of ordinary skill in the art will appreciate that there are multiple parameters which can be used as measures or signs of decreased blood flow, as well as multiple techniques to determine decreased blood flow.

The term "topical application," as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous."

As used herein, the term "treating" may include prophylaxis of the specific injury, disease, disorder, or condition, or alleviation of the symptoms associated with a specific injury, disease, disorder, or condition and/or preventing or eliminating said symptoms if specifically stated as being a prophylactic treatment. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

As used herein "wound" or "wounds" may refer to any detectable break in the tissues of the body, such as injury to skin or to an injury or damage, or to a damaged site associated with a disease or disorder. Although the terms "wound" and "injury" are not always defined exactly the same way, the use of one term herein, such as "injury", is not meant to exclude the meaning of the other term.

The term "xylan" generically encompasses a wide variety of highly complex polysaccharides that are found in plant cell walls and some algae. Xylans are polysaccharides made from units of xylose (a pentose sugar).

CHEMICAL DEFINITIONS

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from two to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from two to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term ($C_5$-$C_8$ alkyl)aryl refers to any aryl group which is attached to the parent moiety via the alkyl group.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

A "meroxapol" is polyoxypropylene-polyoxyethylene block copolymer with the general formula $HO(C_3H_6O)_a(C_2H_4O)_b(C_3H_6O)_aH$. It is available in different grades. Each meroxapol name is followed by a code number according to the average numerical values of the respective monomers units denoted by "a" and "b".

As used herein, the term "optionally substituted" refers to from zero to four substituents, wherein the substituents are each independently selected. Each of the independently selected substituents may be the same or different than other substituents.

A "poloxamer" is a nonionic polyoxyethylene-polyoxypropylene block copolymer with the general formula $HO(C_2H_4O)_a(C_3H_6O)_b(C_2H_4O)_aH$. It is available in different grades, which vary from liquids to solids. Each poloxamer name is followed by a code number according to the average numerical values of the respective monomers units denoted by "a" and "b".

A "poloxamine" is a polyoxyethylen-polyoxypropylene block copolymer of ethylene diamine with the general formula $[HO(C_2H_4O)_a(C_3H_6O)_bC_3H_6]_2NCH_2CH_2N—[C_3H_6(OC_3H_6)_b(OC_2H_4)_aOH]_2$. It is available in different grades. Each poloxamine name is followed by a code number according to the average numerical values of the respective monomers units denoted by "a" and "b".

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

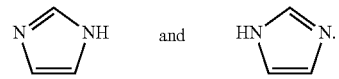

The terminology used herein is for the purpose of describing the particular versions or embodiments only, and is not intended to limit the scope of the present invention. All publications mentioned herein are incorporated by reference in their entirety.

EMBODIMENTS

The present invention provides a novel, specific combination and ratio of different natural polymers, and order of their combination, that allows for thermally-responsive behavior and delivery of active therapeutic agents including, for example, biologically active proteins and/or peptides. The natural polymers used include a combination of xylan and chitosan.

In one embodiment, the polymer composite remains a viscous liquid for more than 2 hours at room temperature after the salt solution is added. This allows for addition of the desired mass of growth factors, etc., and ample time to complete the surgical procedures. Once the polymer solution reaches physiological temperature it undergoes a phase change to become a solid gel in less than 10 minutes. This system allows for a known mass of therapeutic agent(s) to be accurately delivered to injuries of complex shape. In situ gelling lets the material match the complex geometries of injuries that prefabricated scaffolds and carriers are unlikely to match. The material is delivered with commonly used techniques, requiring, in one aspect, only a common syringe to administer the liquid solution to the correct target area. This gelling material can be used in combination with current surgical techniques without disrupting the procedure. For example, a non-union fracture is usually fixed in place with titanium rods or fixation plates. The thermally-responsive composite hydrogel of the invention can be injected after placement of the more traditional healing aids, filling in the areas of likely non-union to accurately provide a precise dose of growth factor and medium in which the cells can move and bridge the defect.

The only products used in current surgical practice for delivery of protein (BMP-2) are flimsy collagen carriers that are little more than wet sponges (Infuse by Medtronic). They are hard to handle and do not provide surgeons with confidence that they are accurately delivering precise amounts of protein. Other materials used in research settings include non-degradable bone cement pastes loaded with proteins which are not acceptable in fracture healing situations and pre-fabricated polymeric scaffolds that do not match injury geometry without milling and grinding. The closest product to the material described in this document is the pure chitosan thermogel that served as the basis for this innovation, but does not allow desirable tissue growth and cellular penetration in the area where it is delivered. The thermo-gelling solution comprising chitosan and xylan described herein meets all of the challenges brought forward by these alternative technologies.

The thermally-sensitive thermo-gelling composite hydrogel of the invention has the potential to have immediate impact in clinical practice due to the non-disruptive nature of its delivery method and the success already seen in delivering active BMP-2, the only effective FDA approved bone morphogenetic protein. The different components could either be sold as a kit (two polymers, small volume of acetic acid, small volume of salt solution) for a longer shelf-life, or for a product with shorter shelf-life but easier to use, a kit could be sold with some components pre-mixed (composite polymer liquid solution, small volume of salt solution). The clinician would simply open up the kit, use the relevant amount of material, then discard the relatively small amount of waste.

Other current products such as Infuse (by Medtronic) used to deliver BMP-2 come in similar fashion with protein already loaded into the matrix. This limits the clinician's ability to customize the treatment for the patient and decreases confidence in the dose of therapeutic agent that is actually delivered. The composite thermogel described here allows for personalized treatment with therapeutic agents chosen by the clinician.

One application of this material is for tissue engineering, to provide a medium for tissue and cellular growth and to provide a carrier for delivery of therapeutic agents (proteins, drugs, etc). The polymer solution can be mixed at least 24 hours before treatment; however the addition of the salt and therapeutic agents can be delayed until immediately before treatment because the addition of salt also speeds up the gelation process. This allows tailored doses of the therapeutic agents to be added for different patients and easy last minute changes to take place if needed. At the time of treatment, the salt solution would be added, and if desired a material, compound, therapeutic agent, etc., is added, then the thermogelling-solution would be injected by syringe at the injury site or applied by any method encompassed by the invention.

In one embodiment, the invention provides compositions and methods for the preparation of a thermo-gelling solution comprising xylan, chitosan, and salt, which has wide applications such as an injectable solution for controlled and prolonged delivery of drugs, proteins and growth factors, a tissue adhesive, a wound dressing material, injectable fillers, injectable composites, and as scaffolds for tissue engineering applications.

In one embodiment of the invention, thermo-gelling composite systems are useful as, injectable compositions for various applications. The compositions can be developed mixing insoluble solid particulates with a chitosan/xylan-inorganic phosphate mixture, or by mixing water-soluble polymer solutions with chitosan/xylan-inorganic phosphate mixture.

In one embodiment, the invention provides a non-toxic, biodegradable, biocompatible and rapidly curing system at physiological temperature to use in a clinical or operating room setting.

In one embodiment, the invention provides a temperature induced rapidly curing multi-component solution which can solidify into a biodegradable gel for various applications.

In one embodiment, the invention provides a temperature induced rapidly curing system which can be used to develop novel blends or composite systems.

In one embodiment, the invention provides a temperature induced rapidly gelling polymer system as an injectable matrix for the controlled and prolonged delivery of drugs, growth factors, therapeutic proteins and peptides.

In one embodiment, the invention provides a method for preparing thermogelling chitosan/xylan solutions with variable gelation times. In one aspect, the gelation times are as short as about several minutes. In another aspect, the gelation times are from about 30 minutes to about several hours. In yet another aspect of the invention, gelation times range from about several hours to about 24 to 36 hours. In one aspect, gelation occurs in less than about 1 hour when the temperature of the thermogelling solution is raised to about 37° C. In another aspect, gelation occurs in less than about 30 minutes when the temperature of the thermogelling solution is raised to about 37° C. In yet another aspect, gelation occurs in less than about 10 minutes when the temperature of the thermogelling solution is raised to about 37° C. In a further aspect, gelation occurs in less than about 5 minutes when the temperature of the thermogelling solution is raised to about 37° C.

In one embodiment, the invention provides a temperature induced rapidly gelling polymer system as an injectable scaffold for various tissue engineering applications.

In one embodiment, the invention provides a temperature induced rapidly gelling polymer system as an injectable cell encapsulation system for various applications.

In one embodiment, the invention provides variable gelling time from a few minutes to a few hours depending on the kind of application the material is targeted.

In one embodiment, the invention provides a method to develop hydrogel systems having different water content and gel strength depending on the kind of application for which the thermo-gelling solution is targeted.

In one embodiment, the invention provides a method to develop cross-linked systems having different architecture such as foams, spheres, fibers.

In one embodiment, the invention provides novel delivery systems. In one aspect, the present invention provides methods and composition for delivering cells, nucleic acids, genes, matrix materials, drugs, proteins, therapeutic agents and other compounds. Delivery of bioactive molecules such as nucleic acid molecules encoding a protein can be significantly enhanced by immobilization of the bioactive molecule in a composition of the invention adjacent to the cells where delivery is desired.

In one embodiment, the invention provides methods for administering novel delivery systems. In one aspect, the novel delivery systems are administered to treat injuries, diseases, disorders, and conditions in subjects in need thereof. In one aspect, the invention is useful for treating a musculoskeletal-associated injury, disease or disorder. Musculoskeletal-associated injuries, diseases or disorders are described herein or are known in the art. In one aspect, the method is useful for enhancing bone repair. In another aspect, the method is useful for treating a bone-associated disease or disorder. In one aspect, treatment of a bone-associated injury, disease or disorder can be done in conjunction with a surgical procedure. In one embodiment, the present invention provides methods and compositions for fabricating three-dimensional structures. In one aspect, the present invention provides various fabrication techniques. One of ordinary skill in the art would appreciate that various fabrication techniques are available to practice the methods of the invention.

In one embodiment, the present invention provides compositions and methods for tissue regeneration. In one aspect, the tissues are selected from the group consisting of bone and spine.

In one embodiment, the compositions and methods of the invention are useful for tissue engineering.

In one embodiment, the compositions and methods of the invention are useful for preparing composites with organic or inorganic components.

In one embodiment, the compositions and methods of the invention are useful in cell and tissue culture systems. In one aspect, the invention provides methods for encapsulating cells.

The skilled practitioner, practicing the invention, could find wide applications for this thermo-gelling solution. Such applications include use as scaffolds for tissue engineering applications, as tissue adhesive, as a wound dressing material, as injectable fillers or composites, and as an injectable solution for controlled and prolonged delivery of drugs, proteins, and growth factors. The invention provides advantages of a workable, flowable, injectable liquid at colder temperatures along with the advantages of a biocompatible viscous gel at higher, physiological temperatures. The teachings of the present invention also overcome limitations of the prior art by providing for simple, mild, and gentle cross-linking agents at lower concentrations than required by the prior art.

In one embodiment, the salt is not added until the solution is ready for use in a subject.

One aspect of the present invention relates to osteogenic repair and osteogenic devices, and more specifically to synthetic implants which induce osteogenesis in vivo in mammals, including humans. The invention therefore encompasses hydrogels and substrates as described herein. Non-synthetic matrix proteins like collagen, glycosaminoglycans, and hyaluronic acid, which are enzymatically digested in the body, are useful for delivery to bone areas (see U.S. Pat. Nos. 4,394,320; 4,472,840; 5,366,509; 5,606,019; 5,645,591; and 5,683,459) and are suitable for use with the present invention.

Other implantable media and devices can be used to assist, or as supplements to, the use of hydrogels of the invention and substrates for delivery of the cells of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The cells of the present invention can be further combined with demineralized bone material, growth factors, nutrient factors, pharmaceuticals, calcium-containing compounds, anti-inflammatory agents, antimicrobial agents, or any other substance capable of expediting or facilitating bone growth.

Examples of osteoinductive factors suitable for use with the compositions of the present invention include demineralized bone particles, a Bone Morphogenetic Protein (BMP), an osteoinductive extract of demineralized bone matrix, or a combination thereof.

In one aspect, the hydrogels of the present invention are useful for growing cells. In one aspect, they support the proliferation and differentiation of cells selected from the group consisting of stem cells, pluripotent stem cells, committed stem cells, embryonic stem cells, adult stem cells, bone marrow stem cells, bone marrow-derived stem cells, adipose stem cells, umbilical cord stem cells, dura mater stem cells, precursor cells, differentiated cells, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons.

Maintaining cells in culture refers to feeding with the appropriate growth medium when necessary, passaging the cells when necessary, etc.

Other materials may also be added to the hydrogels. Compounds and substances that can provide favorable matrix or mesh characteristics also include drugs and other substances that can produce a therapeutic or other physiological effect on cells and tissues within or surrounding an implant. Any substance may be used. Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Other preferred embodiments involve the use of growth factors, including more than one growth factor, as described herein.

Growth Factors

In one embodiment, an effective amount of at least one growth factor, cytokine, hormone, or extracellular matrix compound or protein useful for enhancing wound healing is administered. In one aspect, a combination of these agents is used. In one aspect, growth factors useful in the practice of the invention include, but are not limited to, EGF, PDGF, GCSF, IL6, IL8, IL 10, MCP1, MCP2, Tissue Factor, FGFb, KGF, VEGF, PLGF, MMP1, MMP9, TIMP1, TIMP2, TGFβ, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In one aspect, the growth factors, cytokines, hormones, and extracellular matrix compounds and proteins are human.

Proteins and other biologically active compounds that can be incorporated into, or included as an additive within, a composition comprising compounds of the present invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention.

Other molecules useful as compounds or substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18. Embodiments involving amino acids, peptides, polypeptides, and proteins may include any type of such molecules of any size and complexity as well as combinations of such molecules.

Osteogenic peptides of the invention include, but are not limited to, L1, L2, L5, L6, L7, L11, L12, L13, L14, L19, R1, R3, R8, and analogs, homologs, and derivatives thereof, as described in U.S. Pat. No. 7,323,542 (International Publication No. WO 03/072593) and U.S. Pat. Pub. No. US 2008/0214468.

Embodiments involving amino acids, peptides, polypeptides, and proteins may include any type of such molecules of any size and complexity as well as combinations of such molecules. Examples include, but are not limited to, structural proteins, enzymes, and peptide hormones. These compounds can serve a variety of functions. In some embodiments, the matrix may contain peptides containing a sequence that suppresses enzyme activity through competition for the active site. In other applications, antigenic agents that promote an immune response and invoke immunity can be incorporated into a construct.

For substances such as nucleic acids, any nucleic acid can be present. Examples include, but are not limited to deoxyribonucleic acid (DNA), ent-DNA, oligonucleotides, aptamers, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the electroprocessed matrix. The nucleic acids can be in any form that is effective to enhance uptake into cells.

The invention includes a therapeutic composition comprising at least one surface active copolymer at about 1%-65% w/w. The therapeutic compositions of the invention may be formulated, for example, as liquids or as stable gels.

The therapeutic compositions of the invention have use in treatment of exposed soft tissue or various injuries, for example, thermal injuries, venous stasis ulcers, diabetic wounds, skin grafts, tissue flaps, microvascular surgery, pressure ulcers.

The route of administration can vary depending on the formulation of the pharmaceutical composition being administered as well as on the site of injury, disease, or disorder being treated. The present invention encompasses any useful means of topical administration of the pharmaceutical compositions of the invention to treat the injuries, diseases, and disorders encompassed by the methods of the invention. In one aspect, the compounds are administered via routes, including, but not limited to, direct, topical, cutaneous, mucosal, nasal, inhalation, oral, and ophthalmic. The means for the administration includes, but is not limited to, a dressing material, extruder, aerosol, spray delivery, iontophoresis, a patch, and a transdermal patch.

The present invention further provides for administration of a compound or additional therapeutic agent of the invention as a controlled-release formulation.

The dosage of the active compound(s) being administered will depend on the condition being treated, the particular compound, and other clinical factors such as age, sex, weight, and health of the subject being treated, the route of administration of the compound(s), and the type of composition being administered (gel, liquid, solution, suspension, aerosol, ointment, lotion, cream, paste, liniment, etc.). It is to be understood that the present invention has application for both human and veterinary use.

The invention further encompasses administration of the pharmaceutical compositions of the invention at different times before and after an injury or surgical procedure, as well as varying the optional additional therapeutic agents and surface active copolymers, such as poloxamers.

Examples of poloxamers include poloxamer-101, -105, -105 benzoate, -108, -122, -123, -124, -181, -182, -182 dibenzoate, -183, -184, -185, -188, -212, -215, -217, -231, -234, -235, -237, -238, -282, -284, -288, -331, -333, -334, -335, -338, -401, -402, -403, and -407. In one aspect, the poloxamer is poloxamer-188. In another aspect, the poloxamer is poloxamer-407.

In one embodiment, the pharmaceutical composition of the invention comprises PluroGel™ (PluroGen, Annapolis, Md.).

In one embodiment, at least one of the surface active copolymers is a meroxapol. Exemplary meroxapols include, but are not limited to, meroxapol 105, 108, 171, 172, 174, 178, 251, 252, 254, 258, 311, 312, and 314.

In one embodiment, at least one of the surface active copolymers is a poloxamine. Exemplary poloxamines include, but are not limited to, poloxamine 304, 504, 701, 702, 704, 707, 901, 904, 908, 1101, 1102, 1104, 1301, 1302, 1304, 1307, 1501, 1502, 1504, and 1508.

In one embodiment, the therapeutic composition is formulated as a liquid or stable gel. The copolymer size may range, for example, from an $M_n$ of about 600 to about 20,000. In another aspect, the copolymer size may range, for example, from an $M_n$ of about 1,000 to about 10,000.

In another embodiment, the present invention encompasses a composition comprising a poloxamer at about 0.1% to about 85% w/w, or about 1% to about 65%, or about 1% to about 50%, or about 5% to about 40%, or about 10% to about 40%. Other surface active copolymers can be used at these concentrations as well.

The surface active copolymers may be prepared at different temperatures depending on the type of formulation being prepared, the route of administration, the site of administration, etc. In one aspect, the surface active copolymer is prepared at a temperature ranging from about 0° F. to about 70° F. In another aspect, the surface active copolymer is prepared at a temperature ranging from about 5° F. to about 50° F. In yet another aspect, the surface active copolymer is prepared at a temperature ranging from about 10° F. to about 40° F.

The composition may further comprise an effective amount of at least one additional therapeutic agents which may be useful for the type of injury, disease, or disorder being treated. Additional therapeutic agents include, but are not limited to, anesthetic, analgesic, antimicrobial, steroid, growth factor, cytokine, and anti-inflammatory agents. Useful anesthetic agents include benzocaine, lidocaine, bupivocaine, dibucaine, mepivocaine, etidocaine, tetracaine, butanilicaine, and trimecaine.

In another aspect, the agent is at least one analgesic. In yet another aspect, the agent is an additional therapeutic drug.

In a further aspect, the additional therapeutic agent is an antimicrobial agent. In one aspect, the antimicrobial agent is an antibacterial agent. In another aspect, the antimicrobial agent is an antifungal agent. In yet another aspect, the antimicrobial agent is an antiviral agent. Antimicrobial agents useful in the practice of the invention include, but are not limited to, silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine. It may be desirable for the antimicrobial to be other than Nystatin.

In another aspect, the agent is selected from aspirin, pentoxifylline, and clopidogrel bisulfate, or other angiogenic, or a rheologic active agent.

In one embodiment, the present invention encompasses a method of treating a site of injury on a subject comprising topically administering a poloxamer to the subject in an amount effective to improve blood flow at the site of injury. In one aspect, the blood flow is microvascular blood flow.

Depending on such things as the type of formulation being prepared, the location to which it is to be applied, and the type of injury, disease, or disorder being treated, other agents can be added to the formulation. For example, other additives may include, a moisturizer, a humectant, a demulcent, oil, water, an emulsifier, a thickener, a thinner, an additional surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and a sunscreen.

In one aspect, the microvasculature has a diameter ranging from about 5 µm to about 100 µm. In another aspect, the vessels have a diameter from about 10 µm to about 50 µm. Vessels encompassed by the treatment of the invention include, but are not limited to, capillaries, arterioles, and venules.

In another embodiment, the present invention provides a method of treating a site of injury on a subject comprising topically administering a poloxamer to the patient in an amount effective to reduce inflammation at the site of injury.

The invention encompasses the preparation and use of pharmaceutical compositions comprising as an active ingredient a compound useful for treatment of decreased blood flow associated with injuries and diseases disclosed herein. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. The present invention further contemplates the use of more than one active ingredient.

In one embodiment, at least two different surface active copolymers are used. In one aspect, at least three different surface active copolymers are used. These combinations may include, for example, one or more poloxamers, one or more meroxapols, and one or more poloxamines.

Compositions of this type are described in U.S. Pat. No. 5,635,540 (Edlich et al.), the contents of which are incorporated herein by reference.

Examples of temperature ranges for preparation include, but are not limited to, from about −20° C. to about 15° C., in another aspect from about −18° C. to about 8° C., and in another aspect, from about −15° C. to about 5° C. These ranges also encompass about 0° F. to about 60° F. One of ordinary skill in the art will understand that the temperatures of preparation can be adjusted based on various criteria, such as the surface active copolymer being used, the amount or concentration being used, the type of formulation being prepared for administration, etc.

In one embodiment of the invention, the poloxamer base comprises 80% polyoxyethylene units and 20% polyoxypropylene units.

One of ordinary skill in the art will appreciate that the formulations, method of preparation, and amount of surface active copolymer used may vary, depending on the type or location of the site to be treated. For example, in one embodiment, a poloxamer, such as poloxamer-188, is mixed with water at a ratio of from 1:0.8 to 1.2 w/w. This ratio can be varied. This combination may be mixed until the powder has been wetted. The mixture may then be placed in a freezer or refrigerator and cooled, preferably for at least 4 hours. While cooling, the mixture will undergo phase transition to a liquid, as demonstrated by Edlich et al. (U.S. Pat. No. 5,635,540). The mixture is then removed from the freezer and warmed to room temperature. Pharmaceutical agents such as antimicrobials and anesthetics can be added at this point, as demonstrated by Edlich et al. (U.S. Pat. No. 5,635,540).

The poloxamer base used in preparing the topical preparation of the present invention is a polyoxyalkylene based polymer based on ethylene oxide and propylene oxide and comprises a series of closely related block polymers that may generally be classified as polyoxyethylene-polyoxypropylene condensates terminated in primary hydroxyl groups. They are formed by the condensation of propylene oxide onto a propylene glycol nucleus followed by condensation of ethylene oxide onto both ends of the polyoxypropylene base. The polyoxyethylene hydrophilic groups on the ends of the molecule are controlled in length to constitute anywhere from 10% to 90% by weight of the final molecule.

The compositions of the present invention may comprise one or more co-additives (e.g., solvent such as water). In one aspect, the concentration of a surface active copolymer (e.g., poloxamer 188) is about 0.01 to about 99.99% w/w. In another aspect, it is about 1 to about 90%. In yet another aspect, it is about 10 to about 80%. In a further aspect, it is about 20% to about 70%. In another aspect, it is about 50%. In a further aspect, it is about 5%.

In another embodiment, a formulation of the invention can be impregnated in a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

Chitosan and Carboxymethyl Chitosan

The present invention further encompasses the use of a thermo-gelling chitosan solution that remains liquid at lower temperatures but gels at higher temperatures and requires a lower concentration of cross-linking agents, to which drugs, macromolecules, anesthetics, antimicrobials, growth factors, and other molecules can be added. The present invention relates to a biocompatible thermo-gelling solution of chitosan and inorganic salts and methods for the preparation of and the use of such a solution. In one aspect, the invention encompasses the use of carboxymethyl chitosan.

Chitosan is an N-deacetylated derivative of chitin which is the structural component of crustacean shells and fungal cell walls, and is obtained at a low cost from sea-food processing (Chitin: Fulfilling a Biomaterials Promise: Eugene Khor, Elsevier, Oxford, UK, 2001). The structure of chitin and chitosan are similar to cellulose where, carbon-2 of the cellulose has acetamide or amino groups, for chitin and chitosan respectively. Chitosan is an inert, hydrophilic, biocompatible, and biodegradable polymer and hence are attractive candidates for biomedical and pharmaceutical applications. Chitosan is currently investigated for various applications such as topical ocular application, as a bioadhesive polymer, penetration enhancer by opening epithelial tight-junctions and as wound dressing (Berger, et al., European Journal of Pharmaceutics and Biopharmaceutics 57 (2004) 19-34).

Various chemically modified chitosan derivatives with unique properties have been developed (Hitoshi et al., Prog. Polym. Sci. 29 (2004) 887-908). The excellent biocompatibility of chitosan, combined with its enzymatic biodegradability, makes chitosan an excellent candidate for various in vivo applications. In addition, the low cost of chitosan and its wide availability as a natural waste product, makes chitosan a very attractive polymer for wide range of applications.

Chitosan has been extensively investigated for developing hydrogels with unique properties, due to the hydrophilicity of the base polymer, and the availability of active cross-linkable groups along the polymer chain. These chitosan hydrogels were found to be excellent candidates for a variety of applications, including, controlled release of bioactive/drug molecules, as cell encapsulation matrices, and as tissue engineering scaffolds. Chemical or covalent cross-linking of chitosan making use of mainly the active amino groups along the polymer chain and ionic cross-linking making use of the cationic nature of chitosan aqueous acid solutions, have been extensively investigated for developing hydrogels for various applications.

The different chemical cross-linking agents reported for chitosan include dialdehydes such as glutaraldehyde, diethyl squarate, oxalic acid, and genipin. Apart from these small molecules, functionalized biopolymers such as poly(ethylene glycol diacrylate), oxidized cyclodextrin, telechelic-PVA, PEG dialdehydes and scleroglucan have also been investigated.

In addition to covalent cross-linking, polyelectrolyte complexes of chitosan with a wide range of anionic polymers mainly chitosan alginate system have been extensively investigated for developing drug delivery systems and porous scaffolds for tissue engineering and wound dressings.

Ionic cross-linking of chitosan has been extensively investigated, because it is a simple and mild process with no auxiliary catalyst requirements, and such a procedure has important ramifications for biomedical applications. Metallic anions such as Mo(VI) and Pt(II) have been extensively investigated for ionic cross-linking. Various anions such as sulfates, citrates, oxalates, polyphosphates, and also calcium phosphate, have been tested for the ability to form ionically cross-linked gels with chitosan. All of these ions induce the formation of pure ionic cross-linking, where the chitosan solution instantaneously becomes a gel in the presence of these ions, due to the spontaneity of the ionic reactions.

Additional Therapeutic Agents and Ingredients

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; and (h) combinations thereof.

In one embodiment, a formulation of the invention contains an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European counterpart). Antimicrobial agents useful for the invention include those directed against the spectrums of gram positive organisms, gram negative organisms, fungi, and viruses.

According to the topical anesthetic embodiment of the present invention, in one aspect, suitable local anesthetic agents having a melting point of 30° to 70° C. are prilocalne, tetracaine, butanilcaine, trimecaine, benzocaine, lidocaine, bupivocaine, dibucaine, mepivocaine, and etidocaine.

Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

A list of the types of drugs, and specific drugs within categories which are encompassed within the invention is provided below and are intended be non-limiting examples.

Antimicrobial Agents Include:

silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine.

Analgesic:

Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Antihypertensive:

Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide; Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Oformine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine.

Anti-Inflammatory:

Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumctone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

The present invention encompasses treatment of various injuries, diseases, and disorders. These include, but are not limited to, thermal injury, skin injury, soft tissue injury, non-healing skin wound, burns, acute wound, chronic wound, scrape, cut, incision, laceration, decubitis, pressure ulcer, chronic venous ulcer, venous stasis ulcer, diabetic ulcer, arterial ulcer, radiation ulcer, traumatic wound, open complicated non-healing wound, body piercing, bite wound, insect bite, insect sting, stab wound, gunshot wound, stretch injury, crush wound, compression wound, fracture, sprain, strain, stroke, infarction, aneurism, herniation, ischemia, fistula, dislocation, radiation, surgery, cell, tissue or organ grafting, and cancer.

Pharmaceutical Compositions and Delivery Form

The formulations of the invention may be prepared in a variety of forms known in the art. Topical administration of the present formulation can be performed by, for example, hand, mechanically (e.g., extrusion and spray delivery) or as a component of a dressing (e.g., gauze or other wound covering). The administration of the formulation directly by hand to a tissue or biomaterial surface is preformed so as to achieve a therapeutic coating, which may be uniform, alone or in combination with an overlying dressing.

In one embodiment, the administration of the formulation mechanically is performed by using a device that physically pushes the composition onto a tissue or biomaterial surface so as to achieve a therapeutic coating, which may be uniform, alone or in combination with an overlying dressing.

Those of ordinary skill in the art will be able to identify readily those pharmaceutical agents that have utility with the present invention. Those of ordinary-skill in the art will also recognize numerous other compounds that fall within the categories and that are useful according to the invention for treating injuries where reduced blood flow occurs.

The invention encompasses the preparation and use of pharmaceutical compositions comprising a compound useful for treatment of various skin related injuries, trauma, diseases, disorders, or conditions described herein, including burns, wounds, surgical incisions, etc. The invention also encompasses other injuries, trauma, associated diseases and disorders other than those of the skin, including, but not limited to, gum diseases and disorders. Such a pharmaceutical composition may consist of the active ingredient alone, in a form suitable for administration to a subject, or the pharmaceutical composition may comprise at least one active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

An obstacle for topical administration of pharmaceuticals to the skin is the stratum corneum layer of the epidermis. The stratum corneum is a highly resistant layer comprised of protein, cholesterol, sphingolipids, free fatty acids and various other lipids, and includes cornified and living cells. One of the factors that limits the penetration rate (flux) of a compound through the stratum corneum is the amount of the active substance which can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The compounds of the invention may be administered to, for example, a cell, a tissue, or a subject by any of several methods described herein and by others which are known to those of skill in the art.

The relative amounts of the active ingredient, the pharmaceutically acceptable carrier, and any additional ingredients in a pharmaceutical composition of the invention will vary, depending upon the identity, sex, age, size, and condition of the subject treated and further depending upon the route by which the composition is to be administered.

In addition to the active ingredient, a pharmaceutical composition of the invention may further comprise one or more additional pharmaceutically active or therapeutic agents. Particularly contemplated additional agents include anti-emetics and scavengers such as cyanide and cyanate scavengers.

Controlled- or sustained-release formulations of a pharmaceutical composition of the invention may be made using conventional technology.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical composition may be optionally combined with other ingredients such as moisturizers, cosmetic adjuvants, antioxidants, chelating agents, bleaching agents, tyrosinase inhibitors, and other known depigmentation agents, surfactants, foaming agents, conditioners, humectants, wetting agents, emulsifying agents, fragrances, viscosifiers, buffering agents, preservatives, sunscreens, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

The present invention encompasses biologically active analogs, homologs, derivatives, and modifications of the compounds of the invention. Methods for the preparation of such compounds are known in the art.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Liquid derivatives and natural extracts made directly from biological sources may be employed in the compositions of this invention in a concentration (w/w) from about 1 to about 99%. Fractions of natural extracts and protease inhibitors may have a different preferred rage, from about 0.01% to about 20% and, more preferably, from about 1% to about 10% of the composition. Of course, mixtures of the active agents of this invention may be combined and used together in the same formulation, or in serial applications of different formulations.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea, and combinations thereof. A particularly preferred preservative is a combination of about 0.5% to 2.0% benzyl alcohol and 0.05% to 0.5% sorbic acid.

The composition may include an antioxidant and a chelating agent which inhibit the degradation of the compound for use in the invention in the aqueous gel formulation. Preferred antioxidants for some compounds are BHT, BHA, alphatocopherol, and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are preferred antioxidant and chelating agent respectively for some compounds, other suitable and equivalent antioxidants and chelating agents may be substituted therefor as would be known to those skilled in the art.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Other components such as preservatives, antioxidants, surfactants, absorption enhancers, viscosity enhancers or film forming polymers, bulking agents, diluents, coloring agents, flavoring agents, pH modifiers, sweeteners or taste-masking agents may also be incorporated into the composition. Suitable coloring agents include red, black, and yellow iron oxides and FD&C dyes such as FD&C Blue No. 2, FD&C Red No. 40, and the like. Suitable flavoring agents include mint, raspberry, licorice, orange, lemon, grapefruit, caramel, vanilla, cherry grape flavors, combinations thereof, and the like. Suitable pH modifiers include citric acid, tartaric acid, phosphoric acid, hydrochloric acid, maleic acid, sodium hydroxide, and the like. Suitable sweeteners include aspartame, acesulfame K, thaumatic, and the like. Suitable taste-masking agents include sodium bicarbonate, ion-exchange resins, cyclodextrin inclusion compounds, adsorbates, and the like.

Absorption enhancers for use in accordance with the present invention include, for example, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In certain preferred embodiments, the absorption enhancer is triacetin. In certain preferred embodiments wherein an absorption enhancer is included in the formulation, the absorption enhancer is included in an amount of from about 0.001% to about 10% by weight of the formulation, preferably in an amount of about 0.01% to about 5% by weight of the formulation.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

The present invention may be embodied in other specific forms without departing from the spirit or essential attributes thereof. This invention encompasses all combinations of the different aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

The examples provided throughout his application are non-inclusive unless otherwise stated. They include but are not limited to the recited examples.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type, and age of the subject, etc.

The invention also provides a pharmaceutical pack or kit comprising one or more containers filled with one or more of the ingredients of the pharmaceutical compositions of the invention. Preferably, the subject is a human. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Although any methods and materials similar or equivalent to those described herein can be used in the practice or testing of the present invention, the preferred methods and materials are described herein.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof.

Other methods useful for the practice of the present invention can be found in WO 2009/025955 (Nair et al.) and WO 2007/087350 (Laurencin et al.).

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Example 1

Previous Success of Thermogel Bone Craft Substitutes Made from Chitosan

A thermally-sensitive hydrogel (thermogel) graft substitute made from ultrapure chitosan has been previously used to treat critical sized unicortical defects in a rat femur. The thermogel successfully delivered osteogenic peptides R1 and L7 that induced healing over an 8 week time period (FIG. 1). See the R1, L7, and other osteogenic peptides in U.S. Pat. No. 7,323,542 (International Publication No. WO 03/072593) and U.S. Pat. Pub. No. US 2008/0214468. Osteogenic peptides that were discovered in this laboratory were mixed into the thermogel before delivery with a syringe. While the thermally-responsive material was still in its liquid state, growth factors were mixed into solution. The viscous solution was then injected into the defect area with a syringe where it became a solid gel within ten minutes of being heated to physiological temperature.

Figure 2:
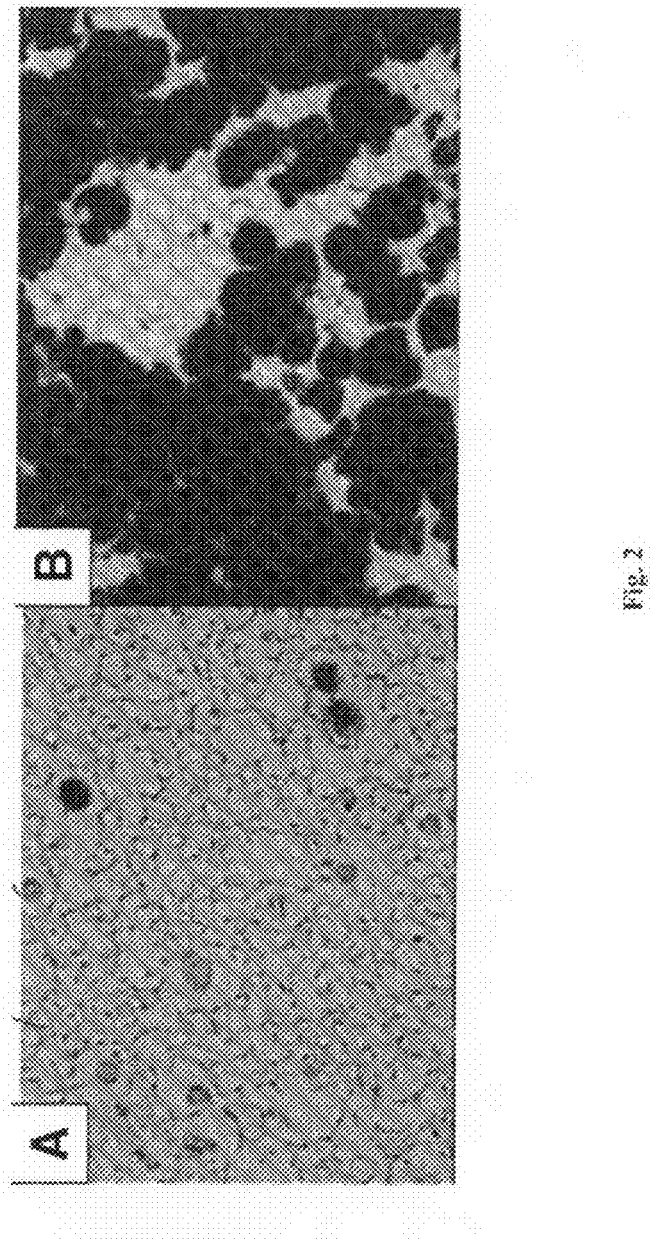
FIG. 2, comprising FIGS. 2A-2B, demonstrates micrographically Alizarin red staining of human mesenchymal stem cells encapsulated in pure chitosan (no xylan) thermogels for 28 days, 2A) cultured in basal control media (40×) and 2B) cultured in osteogenic media (40×). Alizarin red stains bound calcium with a red color as a measure of mineralization.

In vitro testing with the chitosan only (no xylan) thermogel has shown that mesenchymal stem cells were able to differentiate into osteoprogenitor cells in contact with the material (FIG. 2). Human mesenchymal stem cells were cultured for 28 days in both control media and osteogenic media to induce differentiation. At 28 days the cells were stained with alizarin red as a measure of mineralization and to show that the stem cells had differentiated inside the chitosan thermogel.

Figure 3:
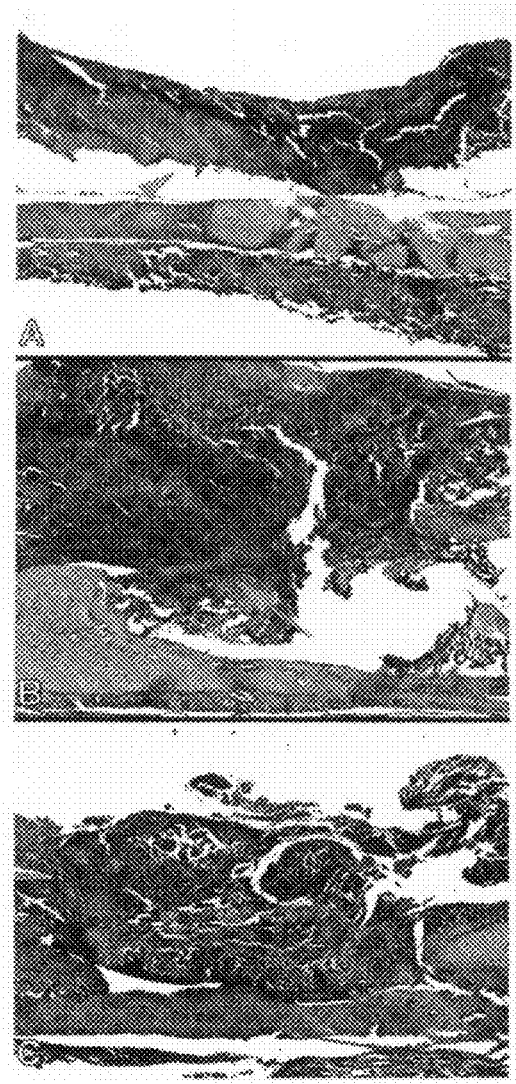
FIG. 3, comprising FIGS. 3A-3B, demonstrates micrographically the results of a degradation study of the pure chitosan (no xylan) thermogel, after: 3A) 1 day; 3B) 2 weeks; and 3C) 4 weeks. The area containing the thermogel remains relatively acellular and devoid of tissue in-growth until the material completely degrades in 4 weeks.
Figure 7:
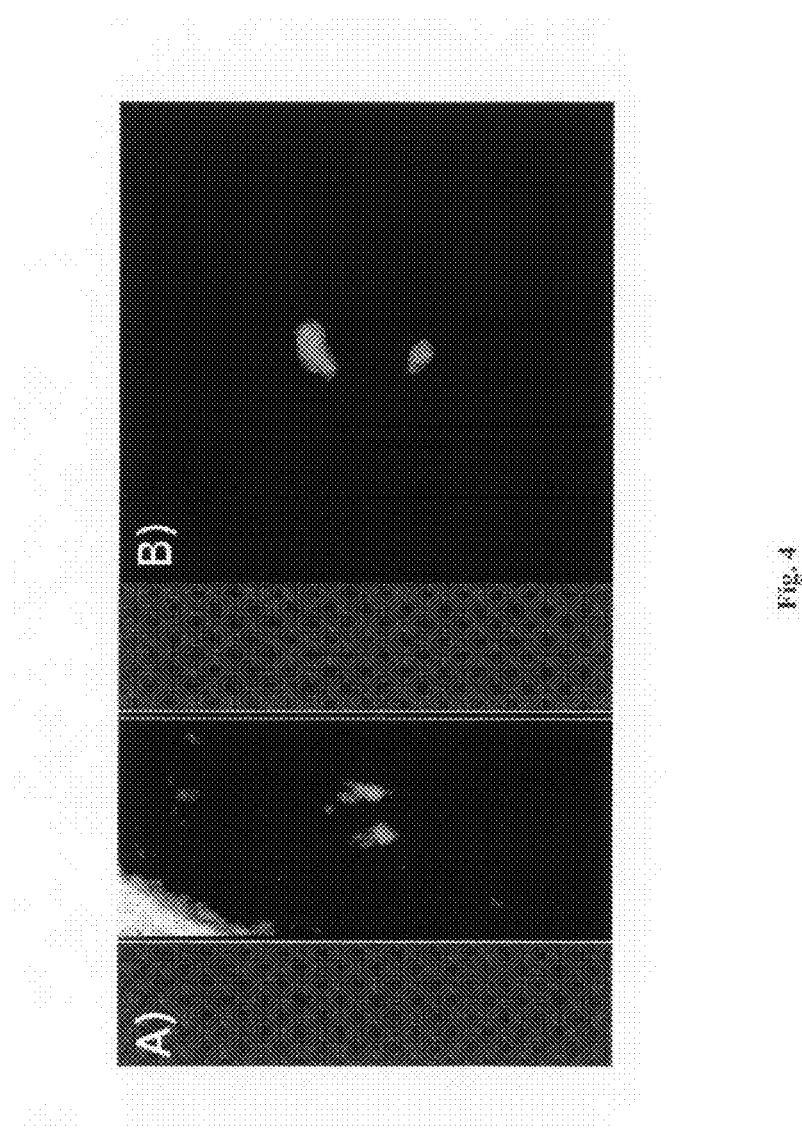

Need for New Material:

The pure chitosan thermogel was successful at delivery of osteogenic factors and allowed differentiation of stem cells within the matrix, however it did not promote in-growth of tissue or cells before degradation. Unless mixed with cells in an in vitro situation, the pure chitosan thermogel does not promote the invasion of cells into the matrix (FIG. 3). A study was performed on the pure chitosan thermogel which showed the beneficial degradation period of 4 weeks within a bone defect. However, the material itself did not allow cells to penetrate into the interior or allow tissue growth into the area until fully degraded. One reason for this is that the chitosan only displays positive charges in the thermogel matrix. This has a large potential to impede the healing at an injury site as cell movement is blocked at the boundary of the hydrogel.

Example 2

Use of Xylan for Preparing and Using Temperature Sensitive Hydrogels In Vivo, Including Delivery of Biologic Compounds A multi-ion environment is more conducive to cell migration within biomaterials. To address this issue, chitosan was blended with another natural polymer, xylan, which is a hemicellulose that displays negative charges on its side chains. Xylan is a plant cell wall polysaccharide containing a backbone of (1-4) linked xylose residues (CAS number: 9014-63-5). Side chains of 4 O methylglucuronic acid and arabinose are present in varying amounts (see glucuronoxylan and arabinoxylan), together with acetyl groups. It is found in the hemicellulose fraction of the wall matrix. The two were first combined as a lyophilized film that could be rehydrated to form a hydrogel. However, as described below, we have modified this material to behave as a thermally-sensitive hydrogel, or thermogel, based on the pure chitosan thermogel.

Natural polymers were chosen because of a large emphasis in engineering circles to increase sustainability in all areas of research from biofuels to biomaterials. Chitosan is already a renewable material as it is found in crustacean shells. Hemicellulose can be up to 50% of the biomass material from plants used as feed stock for biofuels (sugarcane, switchgrass, wood, etc.). However, as hemicellulose is only efficiently degraded by enzymes, it is not an easy product to use for biofuel synthesis. Use of this material in a biomedical technology application, tissue engineering, provides added value for the hard to digest byproducts of biomass production as well as provides tissue engineering applications with an abundant source of renewable and biocompatible material.

Xylan was the hemicellulose of choice herein. The source material for the xylan birchwood (CAS 9014-63-5) and it was purchased from Sigma-Aldrich.

Preparation of a Chitosan/Xylan Thermally-Responsive Hydrogel:

The chitosan/xylan composite thermogel can be prepared in five steps.

A) The desired mass of xylan is made soluble by heating in deionized water at 85° C. for 20 minutes.

B) The xylan solution is cooled to room temperature.

C) Acetic acid is added to create the dilute acid which allows the chitosan to dissolve.

D) The desired mass of ultrapure chitosan is added to the solution and allowed to dissolve overnight. According to the material supplier, the average molecular weight of the chitosan (in acetate salt form) is 429,000 g/mol.

E) When both polymers are in solution, a salt solution is added. This salt is responsible for the phase change that moves the polymer solution from a viscous liquid to a composite hydrogel. It is after this step that time is measured to determine time until gelation.

The two polymers self-associate in solution so that a uniform hydrogel is formed when the phase change takes place. The negative charges on the xylan associate with the positive charges on the dissolved chitosan, binding the two polymers together without need for a separate cross-linking agent.

This thermally-sensitive composite hydrogel can be created with differing ratios of xylan to chitosan. However, there is an upper limit of 1/3 ratio xylan to chitosan (xylan 25% and chitosan 75% of total polymer mass, not total mass of the hydrogel which contains mostly water). If the mass of xylan is increased and exceeds this limit the material no longer behaves as a thermally-sensitive hydrogel and begins to come out of solution as polymeric strands instead of a hydrogel. The total mass of polymer that can be used is described below in the comments on step D.

The specific combination of these materials in this order such that the solution is thermally-sensitive, being a liquid at room temperature and a uniform solid gel at physiological temperature, is the invention. The purpose of the chitosan is to provide a functional base material that forms a gel and is degradable and biocompatible. The purpose of the xylan is to add a degradable and biocompatible source of anions to the cationic environment of a pure chitosan gel. The purpose of the salt is to cause the chitosan to come out of solution, pulling the bound xylan along with it, creating a solid gel.

The measurements were for the hydrogel with the maximum amount of xylan possible (ratio chitosan 3/xylan 1) dissolved in a 0.35% v/v acetic acid solution, using an 85% deacetylated ultrapure chitosan. The average molecular weight of the chitosan (in acetate salt form) is 429,000 g/mol. The mass ratio of components is approximately 1 xylan/3 chitosan/3.75 ammonium hydrogen phosphate salt (AHP). The molarity of ammonium hydrogen phosphate is 15 mmol/L. The total mass of polymers in solution is 16 mg/mL (xylan+chitosan). Added to that is 20 mg/mL AHP salt to start the gelling process.

Comments on Each Synthesis Step:

A) Xylan is not readily soluble in room temperature water. Heating the water increases the solubility of xylan. Without wishing to be bound by any particular theory, it is hypothesized herein that heating breaks down the polymer matrix, such as by breaking down the polymer backbone into smaller polymer segments or by severing polymer cross-links between different polymer strands, or both.

B) These first two steps must be done before the chitosan is added. Chitosan is extremely sensitive to thermal degradation and even at 40° C. will begin to break down. Because chitosan is the operative polymer that we affect for a phase change, preserving its structure is more important than preserving the original hemicellulose structure. Also, pure acetic acid is volatile and so cooling is important before it is added to avoid evaporation of an unknown volume of acid.

C) Addition of an acid is required for the dissolution of chitosan. The acid protonates the $NH_2$ side groups of chitosan, which are not water soluble, to create $NH_3$ groups which are soluble. The volume acid per volume deionized water percentage (v/v) has been shown to be effective between 0.25% and 0.5%. The higher the percentage of acid the more salt must be added to cause a phase change. Therefore, it is desirable to have the percentage acid as low as possible. Acetic acid at 0.5% v/v is sufficient for dissolution of a mass of polymer used to create a hydrogel (defined as a material that is at least 99% water). Acetic acid at 0.25% v/v is effective, but below this the time required for the chitosan to dissolve becomes inconsistent. Acetic acid at 0.35% v/v was used to develop the material as a midpoint between these outer limits.

D) The mass of 85% deacetylated ultrapure chitosan that will dissolve in 0.5% v/v acetic acid in 24 hours was determined to be 16 mg/mL. The mass of 78.9% deacetylated ultrapure chitosan that will dissolve in 0.5% v/v acetic acid in 24 hours was determined to be 14.4 mg/mL. This same mass can reliably be dissolved down to 0.25% v/v acetic acid. The total mass of both polymers (chitosan and xylan) cannot exceed this same limit or precipitation will occur. Both types of chitosan (85% DDA and 78.9% DDA) have been shown to be effective in synthesis of this thermally-responsive composite hydrogel. Because of these two examples, it is assumed that the total mass of chitosan and xylan that can be used is predicted by the mass of pure chitosan that can be dissolved in 24 hours.

E) Both temperature and the amount of salt added affect the amount of time until gelation. The acetic acid creates $NH_3$ side groups to make the chitosan soluble.

The addition of a salt solution removes some or all of these added protons, again creating the insoluble $NH_2$ groups which pull the polymers out of solution, creating the hydrogel. A solution of ammonium hydrogen phosphate (6 grams AHP dissolved in 10 mL deionized water) has been proven to be an effective and non-toxic salt. The phase change happens very slowly at room temperature (about 20 to 25° C.). At physiologically relevant temperatures (near 37° C.) the phase change process happens much more quickly. After addition of 13 μL salt solution per mL polymer solution, the composite will remain a viscous liquid for well over 2 hours at room temperature. This allows for sufficient time to add additional molecules such as proteins, drugs, etc. relevant to the final application. When the temperature of the chitosan/xylan solution is raised to physiological temperature the liquid polymer solution gels in 10 minutes with the same volume of salt solution. This allows the thermogel to match the geometry of its environment in a liquid state, but to gel quickly so the proteins, drugs, etc. are delivered locally where the liquid was placed instead of quickly draining away or being quickly cleared away by biological processes. By increasing the amount of salt added, the time until gelation can be decreased down to seconds. By decreasing the amount of salt added, the time until gelation can be increased to hours. Sodium pyruvate salt has also been shown effective as a gelling salt.

It was stated in Laurencin et al. (U.S. patent application Ser. No. 12/162,057; PCT App. No. PCT/US2007/001896, filed on Jan. 25, 2007) that the chitosan solution is maintained below 10° C., but this is not necessary. Additionally, maintenance of solutions in an ice bath does not appear to be a necessary step when working with the chitosan/xylan composite.

pH of Chitosan/Xylan Hydrogel Compositions

The pH was monitored during preparation of the thermogel material using the maximum amount of xylan possible (ratio of 3 chitosan/1 xylan/3.75 AHP). The pH was followed at various steps:

1. Pure deionized water has a pH of 5.3.
2. The pH of a solution with 0.004 grams of xylan dissolved per mL water is 6.5.
3. The pH of solution #2 also with 0.35% v/v acetic acid added is 3.3.
4. The pH of solution #3 also with 0.012 grams of chitosan per mL dissolved is 4.6.
5. The pH of solution #4 also with 0.015 grams of AHP per mL salt dissolved is 7.0 (within 2 minutes of salt addition the pH rises from the previous 4.6 to 7.0).
6. The pH of the solution in #5 once it has changed phase to a solid gel is 7.2.

The "pH history" using different percentages of acetic acid also resulted in a final pH of 7.0 while in liquid phase at step #5 by adjusting the mass of AHP added. They also rise to 7.2 after the phase change takes place. The pH of a solution with 0.5% v/v acetic acid is 4.3 in step #4. The pH of a solution with 0.25% v/v acetic acid is 4.9 in step #4.

Figure 5:
FIG. 5, comprising FIGS. 5A-5B, demonstrates micrographically results of experiments in which PLGA microsphere scaffolds were filled with: 5A—pure chitosan thermogel; and 5B—the chitosan/xylan thermogel and placed in the thigh muscle of a rat. The chitosan/xylan composite allowed much more tissue penetration (5B) than the pure chitosan thermogel (5A). Both images are magnified at 4×.

Success of Chitosan/Xylan Composite Hydrogel—Gelling and Delivery of Biological Molecules In Vivo:

The new chitosan/xylan composite hydrogel disclosed herein was used to deliver the protein BMP-2 to an ectopic site in a rat. The new graft material, with a chitosan/xylan ratio of 3/1, successfully delivered BMP-2 to the surrounding tissue in rat muscle and created mineralized bone (FIG. 4). When compared to the pure chitosan thermogel, the composite implants showed greater integration of the surrounding tissue (FIG. 5). PLGA microsphere scaffolds were filled with either the pure chitosan thermogel or the new chitosan/xylan composite proposed for use in this study. The scaffolds were placed into the thigh muscle of a rat. After 2 weeks the scaffolds were removed, cut into 8 micron sections and stained with H&E. The surrounding tissue showed much better penetration into the composite hydrogel than was seen with the pure chitosan material.

Example 3

The Effectiveness of the Chitosan/Xylan Hydrogel in Maintaining Viable Cells: Real Time PCR Data Measuring Gene Expression from Mouse Mesenchymal Stem Cells (D1 Cells)

Cell Number:

Real time PCR measurement of 18s gene expression in D1 mouse mesenchymal stem cells (a common gene used as a control that can reveal the difference in relative cell numbers between cultures) showed that cells cultured on the chitosan/xylan composite had much higher expression of this gene compared to the cells cultured on the pure chitosan material with no xylan (real time PCR results: composite 18s: $1.08 \times 10^{-4} \pm 7.42 \times 10^{-6}$; pure chitosan 18s: $3.54 \times 10^{-8} \pm 8.89 \times 10^{-9}$). This does not necessarily mean that growth is 1000 faster, but it does indicate that there are many more cells living on the chitosan/xylan hydrogel after 3 days than on the pure chitosan hydrogel. It also shows a cell population that has more overall metabolic activity in the presence of the chitosan/xylan composite over and above that seen with a pure chitosan thermogel.

Bone Related Gene Expression:

Real time PCR measurements were also made to analyze the expression of the osterix and runx2 genes in these same D1 cells. Osterix and runx2 are transcription factors important in the differentiation of stem cells into osteoblast cells that can heal bone. The results normalized for cell number show that after only 3 days, the bone related gene expression in the cells grown in normal media (DMEM) on the chitosan/xylan composite can match the bone related gene expression of cells grown on tissue culture plastic for 7 days in an osteogenic medium that is designed to increase differentiation of stem cells into bone cells (ODM media). This demonstrates that there is already beneficial gene expression after only 3 days. DMEM is normal cell culture media which should not promote any specific cell changes. After 7 days of cell culture in normal media without the chitosan/xylan hydrogel, the gene expression levels did not rise to levels seen in either of the other two described conditions. These results suggest beneficial roles for this material in tissue engineering applications.

Figure 6:
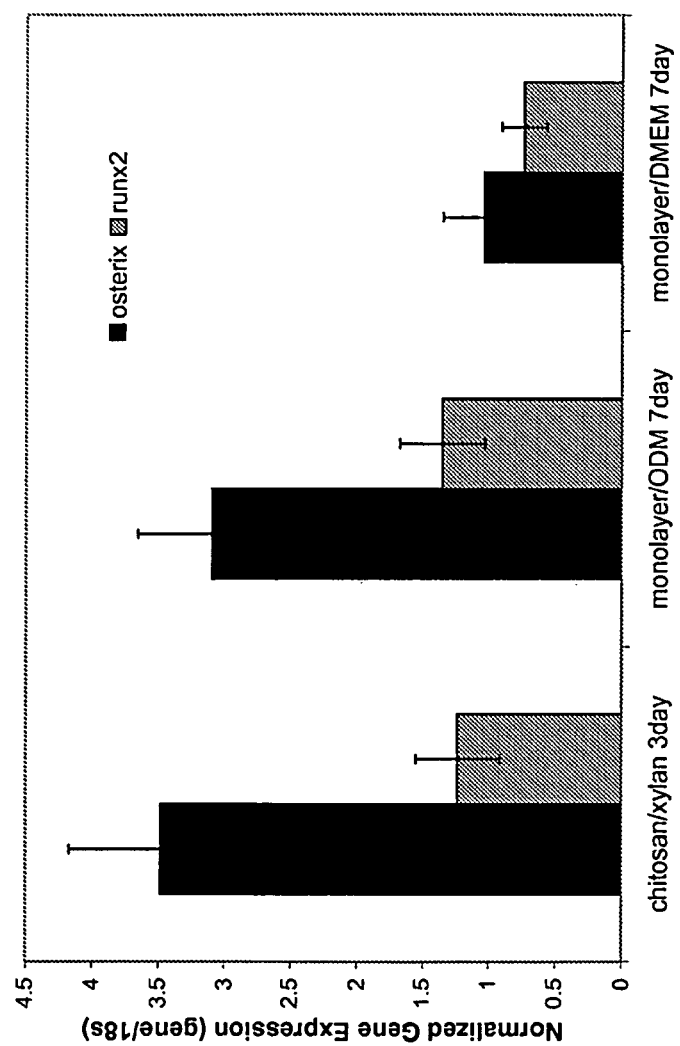
FIG. 6 graphically illustrates Real Time PCR measurement of the expression of the osterix and runx2 genes in D1 stem cells: 1) grown on chitosan/xylan for 3 days; 2) grown in monolayer on tissue culture plastic with osteogenic differentiation medium (ODM) for 7 days; or 3) grown in monolayer on tissue culture plastic with growth medium (DMEM) for 7 days. Gene expression levels were normalized with respect to cell numbers in each culture. The results show that after only 3 days, the D 1 cells grown on the chitosan/xylan composite ("chitosan/xylan 3 day" group) match the bone related gene expression level of D1 cells grown in osteogenic medium (ODM) for an entire week ("monolayer/ODM 7 day" group). The left bar of each of the three groups (black) represents osterix expression, and the right bar represents runx2 expression. The ordinate represents normalized gene expression, based on gene/18s.

See FIG. 6, which demonstrates real time PCR measurement of the expression of the osterix and runx2 genes. Gene expression levels were normalized with respect to cell numbers in each culture, based on 18s.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Nair, L S & Laurencin, C T, U.S. Patent Appl. 60/705,812.
2. Nair L S, et al. "Development of injectable thermogelling chitosan-inorganic phosphate solutions for biomedical applications," BIOMACROMOLECULES 8(12), 3779-3785 (2007).
3. Chemte A, et al. "Novel injectable neutral solutions of chitosan form biodegradable gels in situ," Biomaterials 21(21), 2155-2161 (2000).
4. Gabrielii I, P. Gatenholm P. "Preparation and properties of hydrogels based on hemicellulose," Journal of Applied Polymer Science 69, 1661-1667 (1998).
5. Gabrielii I, et al. "Separation, characterization and hydrogel-formation of hemicellulose from aspen wood," CARBOHYDRATE POLYMERS 43(4), 367-374 (2000).
6. Tanodekaew S, et al. "Xylan/polyvinyl alcohol blend and its performance as a hydrogel," Journal of Applied Polymer Science 100(3), 1914-1918 (2006).
7. Hansen N M L, and Plackett D. "Sustainable Films and Coatings from Hemicelluloses: A Review," Biomacromolecules 9(6), 1493-1505 (2008).
8. Ebringerova A, et al. "Hemicellulose," Advances in Polymer Science 186, 1-67 (2005).
9. Muzzarelli R A A. "Chitins and chitosans for the repair of wounded skin, nerve, cartilage and bone," Carbohydrate Polymers 76(2), 167-182 (2009).
10. Muzzareli R A A, and Muzzarelli C. "Chitosan chemistry: Relevance to the biomedical sciences," Advances in Polymer Science 186, 151-209 (2005).

What is claimed is:

1. A thermo-gelling solution comprising xylan, chitosan, a salt, and an acid, wherein when prepared said thermo-gelling solution is a solution at a pH between about 6.0 and about 8.0 and at a temperature below about 30° C., further wherein when the temperature is increased gelation of said solution occurs more rapidly or when the salt is added gelation occurs more rapidly, and wherein the ratio of chitosan to xylan is about 3 to 1 by weight.

2. The thermo-gelling solution of claim 1, wherein when said chitosan is 85% deacetylated ultrapure chitosan, the total amount of chitosan and xylan added is about 16 mg/ml.

3. The thermo-gelling solution of claim 1, wherein when said chitosan is 78.9% deacetylated ultrapure chitosan, the total amount of chitosan and xylan added is about 14.4 mg/ml.

4. The thermo-gelling solution of claim 1, wherein said gelation occurs within a temperature range from about 37° C. to about 50° C.

5. The thermo-gelling solution of claim 4, wherein said gelation occurs at about 37° C.

6. The thermo-gelling solution of claim 1, wherein said gelation occurs in less than about 1 hour when the temperature of said thermogelling solution is increased to about 37° C.

7. The thermo-gelling solution of claim 6, wherein said gelation occurs in less than about 30 minutes when the temperature of said thermogelling solution is increased to about 37° C.

8. The thermo-gelling solution of claim 7, wherein said gelation occurs in less than about 10 minutes when the temperature of said thermogelling solution is increased to about 37° C.

9. The thermo-gelling solution of claim 8, wherein said gelation occurs in less than about 5 minutes when the temperature of said thermogelling solution is increased to about 37° C.

10. The thermo-gelling solution of claim 1, wherein said salt is an inorganic salt.

11. The thermo-gelling solution of claim 1, wherein said salt is ammonium hydrogen phosphate or sodium pyruvate.

12. The thermo-gelling solution of claim 11, wherein when said salt is ammonium hydrogen phosphate, said solution comprises a ratio of chitosan to ammonium hydrogen phosphate between about 1.0 and about 3.5.

13. The thermo-gelling solution of claim 11, wherein when said salt is ammonium hydrogen phosphate, the concentration of said salt is about 20 mg/ml and the molarity of said salt is about 15 mmol/l.

14. The thermo-gelling solution of claim 1, wherein said solution further comprises an aqueous acidic solution.

15. The thermo-gelling solution of claim 1, wherein said solution comprises acetic acid at a concentration from about 0.25% v/v to about 0.5% v/v.

16. The thermo-gelling solution of claim 1, wherein said chitosan has a molecular weight of between about 20,000 and about 500,000.

17. The thermo-gelling solution of claim 16, wherein said chitosan has a molecular weight of about 429,000.

18. The thermo-gelling solution of claim 1, wherein said solution is biocompatible.

19. A pharmaceutical composition comprising the thermo-gelling solution of claim 1, a pharmaceutically-acceptable carrier, and optionally an effective amount of at least one cell, material, drug, therapeutic agent, or compound useful for treating an injury, disease, or disorder.

* * * * *

UNITED STATES PATENT AND TRADEMARK OFFICE
CERTIFICATE OF CORRECTION

PATENT NO. : 8,623,403 B2  
APPLICATION NO. : 13/512250  
DATED : January 7, 2014  
INVENTOR(S) : Bush Page 1 of 1

It is certified that error appears in the above-identified patent and that said Letters Patent is hereby corrected as shown below:

On the title page, Item [57] Line 2, delete "thereto-gelling" and insert -- thermo-gelling --, therefor.

Signed and Sealed this  
Sixteenth Day of September, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,623,403 B2 | Page 1 of 1 |
| APPLICATION NO. | : 13/512250 | |
| DATED | : January 7, 2014 | |
| INVENTOR(S) | : Joshua R. Bush | |

It is certified that error appears in the above-identified patent and that said Letters Patent is hereby corrected as shown below:

In the specification

In column 1, line 14, after "entirety.", insert --¶STATEMENT OF GOVERNMENT INTEREST This invention was made with government support under AR050960 awarded by the National Institutes of Health. The government has certain rights in the invention.--, therefor Signed and Sealed this
Third Day of May, 2016

Michelle K. Lee
*Director of the United States Patent and Trademark Office*